(12) United States Patent
Weisenberger et al.

(10) Patent No.: US 7,209,579 B1
(45) Date of Patent: Apr. 24, 2007

(54) ANATOMIC AND FUNCTIONAL IMAGING OF TAGGED MOLECULES IN ANIMALS

(75) Inventors: Andrew G. Weisenberger, Yorktown, VA (US); Stanislaw Majewski, Grafton, VA (US); Michael J. Paulus, Knoxville, TN (US); Shaun S. Gleason, Knoxville, VA (US)

(73) Assignee: Jefferson Solence Ass. LLC, Newport News, VA (US)

( * ) Notice: Subject to any disclaimer, the term of this patent is extended or adjusted under 35 U.S.C. 154(b) by 865 days.

(21) Appl. No.: 10/341,715

(22) Filed: Jan. 14, 2003

(51) Int. Cl.
*G06K 9/00* (2006.01)
(52) U.S. Cl. .................. 382/128; 382/129; 382/130; 382/131; 382/132; 382/133; 382/134
(58) Field of Classification Search ......... 382/128–134
See application file for complete search history.

(56) References Cited

U.S. PATENT DOCUMENTS 6,490,476 B1 * 12/2002 Townsend et al. .......... 600/427
6,666,579 B2 * 12/2003 Jensen ....................... 378/197
2004/0002641 A1 * 1/2004 Sjogren et al. ............. 600/407

* cited by examiner

*Primary Examiner*—Matthew C. Bella
*Assistant Examiner*—Shefali Patel

(57) ABSTRACT

A novel functional imaging system for use in the imaging of unrestrained and non-anesthetized small animals or other subjects and a method for acquiring such images and further registering them with anatomical X-ray images previously or subsequently acquired. The apparatus comprises a combination of an IR laser profilometry system and gamma, PET and/or SPECT, imaging system, all mounted on a rotating gantry, that permits simultaneous acquisition of positional and orientational information and functional images of an unrestrained subject that are registered, i.e. integrated, using image processing software to produce a functional image of the subject without the use of restraints or anesthesia. The functional image thus obtained can be registered with a previously or subsequently obtained X-ray CT image of the subject. The use of the system described herein permits functional imaging of a subject in an unrestrained/non-anesthetized condition thereby reducing the stress on the subject and eliminating any potential interference with the functional testing that such stress might induce.

5 Claims, 5 Drawing Sheets

– – – – LINEAR SWEEP LIMITS
– – – – CAMERA FOV LIMITS

ANATOMIC AND FUNCTIONAL IMAGING OF TAGGED MOLECULES IN ANIMALS

The United States of America may have certain rights to this invention under Management and Operating Contract No. DE-AC05-84ER40150 from the Department of Energy.

FIELD OF THE INVENTION

The present invention relates to methods and apparatus for the in vivo detection of tagged molecules in animals, especially small animals of the type used in laboratory studies, without the use of anesthetics and their attendant risks.

BACKGROUND OF THE INVENTION

Currently, the detection and imaging of tagged molecules in small animals, requires that the animal be rendered unconscious through the inhalation or injection of anesthetics or alternatively, physically restrained. These procedures are inherently undesirable because of the likelihood that the anesthesia or restraint will introduce complicating factors to the biological phenomenon under study. This is particularly an issue in neurological and brain function studies that are being done with small animals such as rats and mice. In addition, there is a substantial risk that the animal will be killed by the procedure, which event can carry a high cost in time resources and the overall effort, especially when the animal under study has been specially bred. Also, if several studies are planned for the same animal, it is not possible to subject the animal to too many episodes of anesthesia in a given period of time. In such studies, it is often desirable to follow the functional, metabolic or molecular activity for extended periods of time, extending through phases of animal activity such as sleep, active, etc. depending upon the type of label used to monitor a particular function (for example, uptake, washout times, isotope half life, etc.).

There therefore exists a need for a method and apparatus to perform such studies that does not require the anesthetization or other immobilization of such animals during the performance of such studies with all of the attendant risks to the animal.

OBJECT OF THE INVENTION

It is therefore an object of the present invention to provide a method and apparatus capable of in vivo anatomic and functional imaging of radioisotope and/or optically tagged molecules in non-anesthetized, non-restrained small animals that obviates the foregoing concerns.

SUMMARY OF THE INVENTION

The present invention describes a novel functional imaging system for use in the imaging of unrestrained and non-anesthetized small animals or other subjects and a method for acquiring such images and further registering them with anatomical X-ray images previously or subsequently acquired. The apparatus of the present invention comprises a combination of an IR laser profilometry system and gamma, PET and/or SPECT, imaging system, all mounted on a rotating gantry, that permits simultaneous acquisition of positional and orientational information and functional images of an unrestrained subject that are registered, i.e. integrated, using image processing software to produce a functional image of the subject without the use of restraints or anesthesia. The use of the system described herein permits functional imaging of a subject in an unrestrained/non-anesthetized condition thereby reducing the stress on the subject and eliminating any potential interference with the functional testing that such stress might induce.

DETAILED DESCRIPTION

Figure 1:
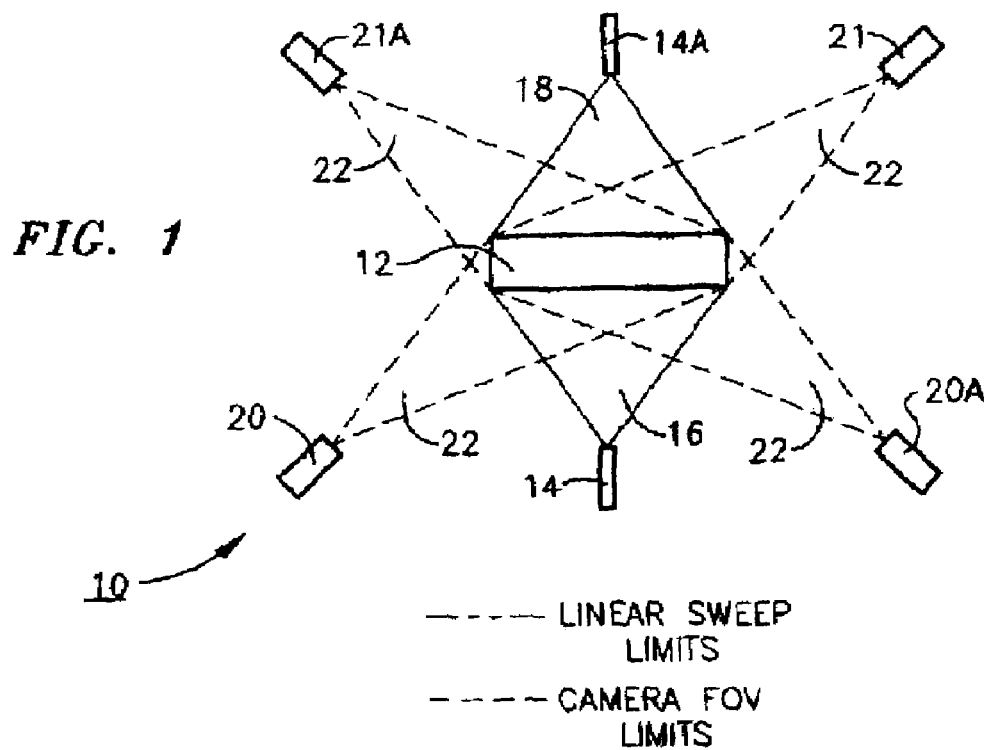
FIG. 1 is a side view of a laser profilometry tracking system and burrow in accordance with one embodiment of the present invention.

The present invention makes use of recent advances in a large number of advanced and sophisticated technologies to provide an imaging system capable of anatomically and/or functionally imaging radioisotopes and/or optically tagged molecules in non-anesthetized and non-restrained small animals. Among the technologies used, are: 1) laser/IR tracking of the animal under study in a relatively open environment such as a tubular containment area or "burrow" or other suitable enclosure using laser/IR tracking devices capable of determining and recording the orientation of an animal under study; 2) imaging labeled biological markers using small gamma, PET or SPECT detectors; and 3) dynamically collecting and reconstructing images normalized to the placement of the radioisotope or optically labeled regions within the animal body as determined by the laser/IR orientation determining devices.

The novel method and apparatus described herein make use of the following state of the art technologies to achieve this capability: 1) compact high resolution gamma imagers for single photon emission tomography (SPECT) imaging and positron emission tomography (PET) imaging; 2) modern IR and laser detection of labels applied to small animals or other subjects to determine their orientation in a specified time interval; 3) advances in radio- and optical labels applied in functional imaging; 4) compact image digital X-ray imaging systems making use of low dosage pulsed X-ray generators to obtain X-ray computed tomography (CT) images; 5) digital camera systems sensitive in the laser emission and IR regions of the spectrum; 6) fast digital signal processing technology; 8) high speed data acquisition and processing technology; and 9) fast image processing technology.

Thus, according to the present invention, a state of the art tracking system comprising: 1) multiple line-shaped IR laser beams that scan across an unrestrained subject, be it a small animal or a human subject, said subject being labeled with IR laser reflective tags; and 2) IR sensitive CMOS (complimentary metal oxide semiconductor) cameras that extract a linear IR laser profile from the information generated by the acquisition of the image generated by an IR laser strobe directed at the subject and the laser light reflected from the reflective tags as the CMOS cameras sweep across the subject, is used to spatially locate and map the body of an unrestrained and non-anesthetized subject, while SPECT or PET images of the subject are acquired. The laser acquired profilometry data and functional images acquired by the SPECT or PET imaging systems are then combined using state of the art software to generate a combined and registered profile and a functional image of the subject. The image thus generated can be further combined, i.e. registered, with a previously or subsequently acquired X-ray or similar image for analytical or diagnostic purposes.

While the apparatus and methods described herein are related primarily to the imaging/examination of small animals, it will be readily recognized that similar apparatus and methods can be applied in the examination/imaging of large animals and humans where, under normal circumstances and using conventional imaging techniques, the particular procedure being performed conventionally requires that the subject remain relatively motionless for some extended period of time, but that anesthesia or immobilization is undesirable or adversely influences the test being performed.

As used herein, the term "imaging volume" is meant to refer to the volume within which the subject is allowed to range or move during the imaging operation. In the case of apparatus suitable for the examination of small animals such as mice or rats the "imaging volume" will generally comprise a "burrow" or tubular structure within which the animal may be allowed to move freely during the imaging operation. In the case of large animals or human, the "imaging volume" will comprise a larger, but well defined volume within which the large animal or human can have free, but perhaps somewhat limited, movement during the imaging operation.

Figure 8:
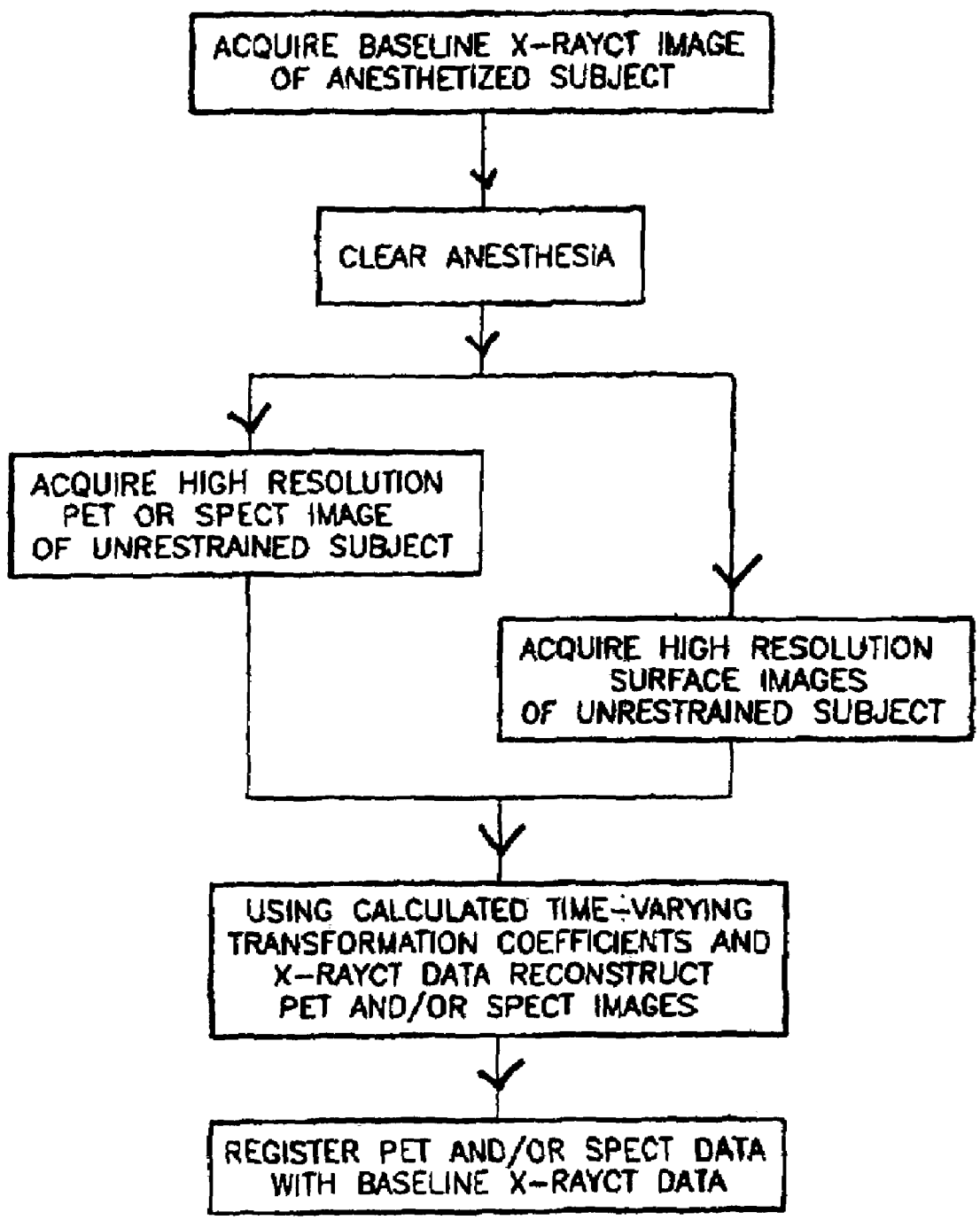
FIG. 8 is a process flow diagram showing the operations used to obtain anatomical and functional images of an unrestrained or non-anesthetized subject in accordance with the method of the present invention.

As shown in FIG. 8, anatomical and functional imaging is achieved in accordance with the present invention by first optionally, but preferably, obtaining an X-ray CT scan of the subject while anesthetized or immobilized. Once the anesthesia has cleared the subject's system, high resolution PET and/or SPECT and high resolution surface images of the unrestrained subject that has been injected or ingested a suitable tracer material are simultaneously acquired. Using calculated time-varying transformation coefficients and laser profilometry data the PET and/or SPECT images are reconstructed. Finally, the PET and/or SPECT mages are registered with the baseline X-ray CT data to provide and integrated functional and anatomical image of the subject under study. While the method shown in FIG. 8 shows obtaining the X-ray CT scan of the subject while anesthetized or immobilized before imaging using the position/location system and SPECT/PET imaging system of the present invention, it will be obvious to the skilled artisan that X-ray imaging of the subject within the imaging volume may also be performed subsequent to the functional imaging with equally satisfactory results.

Referring now to FIG. 1, that depicts the essential elements of the tracking system of the imaging apparatus of the present invention, the tracking system 10 comprises: 1) an "imaging volume", in this case a burrow 12, within which the subject is permitted to range during imaging; 2) a plurality (at least two) of IR-lasers 14 capable of generating linear-shaped laser beams that can be scanned over the entire volume of burrow 12 as depicted by fields of view 16 and 18; and 3) a plurality of IR-sensitive CMOS cameras 20 and 20A and 21 and 21A that together are capable of imaging the entire volume of burrow 12 as depicted by fields of view 22. While the description herein is provided in the context of the use of CMOS IR sensitive cameras due to the inherent heightened sensitivity and accuracy of such devices, it will be apparent tot the skilled artisan that as suitable IR sensitive camera, such as an IR sensitive CCD camera could also be applied to obtain a useful albeit somewhat less accurate imaging system.

Figure 2:
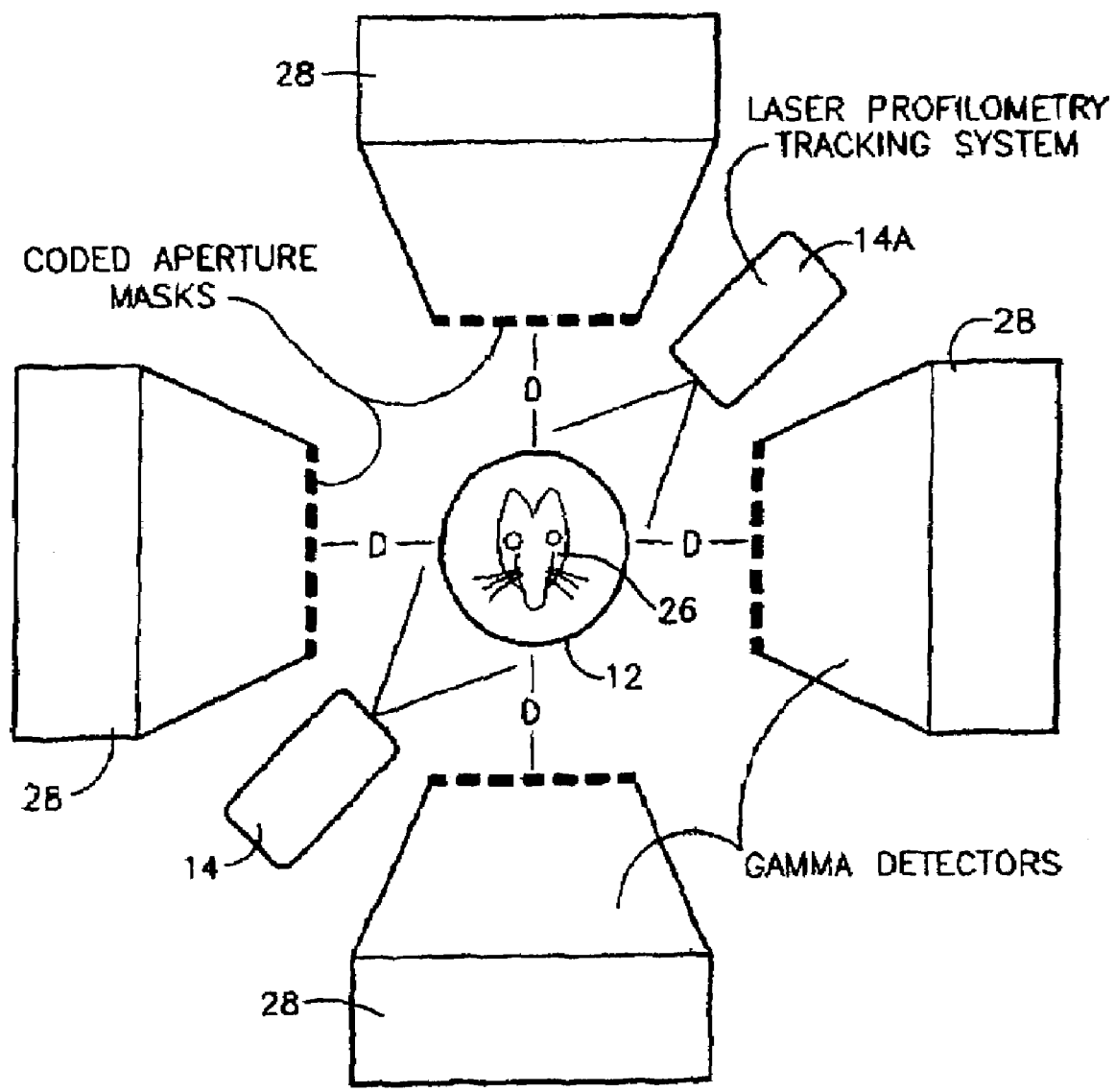
FIG. 2 is an end view of the apparatus depicted in FIG. 1.

The foregoing arrangement of elements is seen from a different angle in the view depicted in FIG. 2. As shown in FIG. 2, the apparatus of the present invention may include, in addition to the lasers 14 and gamma detectors 28 that can rotate about burrow 12 as described hereinafter, cages 12A and 12B at either end of burrow 12 that provide an volume for free range of the subject animal. Cages 12A and 12B may be carried on supports 40 and 42, if desired to properly orient cages 12A and 12B in the complete apparatus structures depicted in FIGS. 6 and 7 described below.

Tracking is accomplished using a two-staged approach where, in stage 1, extrinsic landmark points, IR-laser reflectors or markers, not shown, are applied to the animal, for example at the skull, scapula, spine, ribs, pelvis and limb joints, and then imaged to allow quick extraction of the position of the critical anatomic features. In stage 2, a time dependent surface of the animal is acquired that is subsequently used to accurately determine the position and pose of the animal during the study operation. An IR strobe integral to lasers 14 and invisible to the animal is used in conjunction with CMOS cameras 20, 20A, 21 and 21A to image the position of these markers or reflectors. The IR markers are easily segmented from the acquired images so that the position of the various skeletal features can be determined. These extracted skeletal markers indicate roughly where the rest of the body tissue is located. This is especially true for the head, thorax pelvic area and limbs. The reflective landmark points are also radio-opaque so that they are visible in X-ray CT volume of the anesthetized animal taken prior or subsequent to any SPECT or PET imaging study. Thus, these points will be easily detectable in both the laser surface profile surface data and the X-ray CT volume so that a fast, yet roughly accurate initial registration of the two data sets can be performed. The IR marker/reflectors are strobed and imaged by CMOS cameras 20, 20A, 21 and 21A between the laser profile scans of the animal surface. Given the frequency of laser scans that is possible (~150 msec/scan) the animal markers can be imaged approximately every 200 msec (5 times/sec.).

Figure 6:
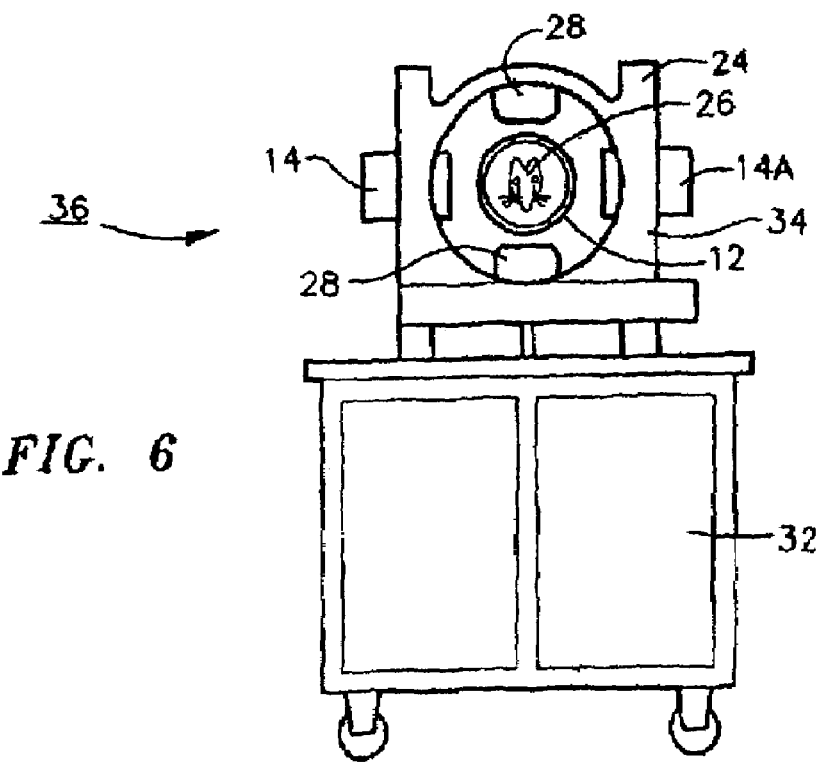
FIG. 6 is a front elevation showing the configuration of one embodiment of the imaging apparatus of the present invention using two detector heads.
Figure 7:
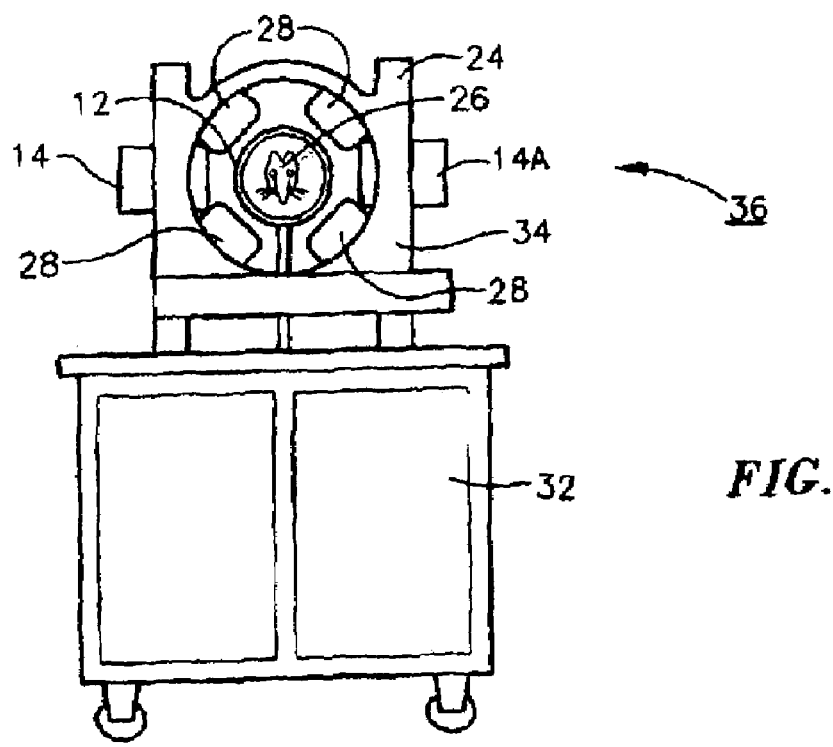
FIG. 7 is a front elevation showing the configuration of an alternative embodiment of the imaging apparatus of the present invention using four detector heads.

A real time representation of the outer surface of the subject is generated using a commercially available laser profilometry system consisting of two linear laser profile generators 14 and four "smart" CMOS cameras 20, 20A, 21 and 21A. The CMOS cameras are designated "smart" because the CMOS has an on-chip data processing to extract the laser profile and measure via a triangulation algorithm the height of the object from the acquired images in real time, up to about 200 profiles per second. As shown in FIGS. 6 and 7, the two lasers 14 are mounted on a gantry 34 180° from one another and so that the laser profiles (beams) 16 and 18 can show through the gap between the gamma detectors. Burrow 12 is transparent to IR and preferably coated with an antireflective coating to allow maximum transmission of IR the laser profile. Burrow 12 is also opaque to visible light to avoid visual stimulation of the animal. Each laser 14 and 14A is mounted to a rotating pin (not shown) so the laser profile can be swept along the length of burrow 12 perpendicular to the orientation of the projected laser profile 16 and 18. Two CMOS cameras 20 and 20A are also mounted on the gantry 24 shown in FIGS. 6 and 7 to image the laser profile 16 as it sweeps across one side of the subject. CMOS cameras 20 and 20A are preferably mounted away from the central plane of rotation of so they can view the laser profile 16 at an angle of from about 45° to about 60° from the axis of gantry rotation. A second pair of CMOS cameras 21 and 21A are mounted to image the profile of laser 14A as it sweeps across the opposite side of the subject. Two cameras are needed per side to eliminate surface occlusions. The height information extracted by each camera's on-chip processor is used to build two complete surfaces of the opposite sides of the subject. Because the geometry of the system is fixed, the two surfaces can be straightforwardly aligned and merged into a single data set for later registration to the surface extracted from the X-ray CT volume. While there will be partially incomplete data at the boundary where the two surfaces meet, this will not prevent effective registration of the laser profilometry surface to the extracted X-ray CT surface.

Figure 3:
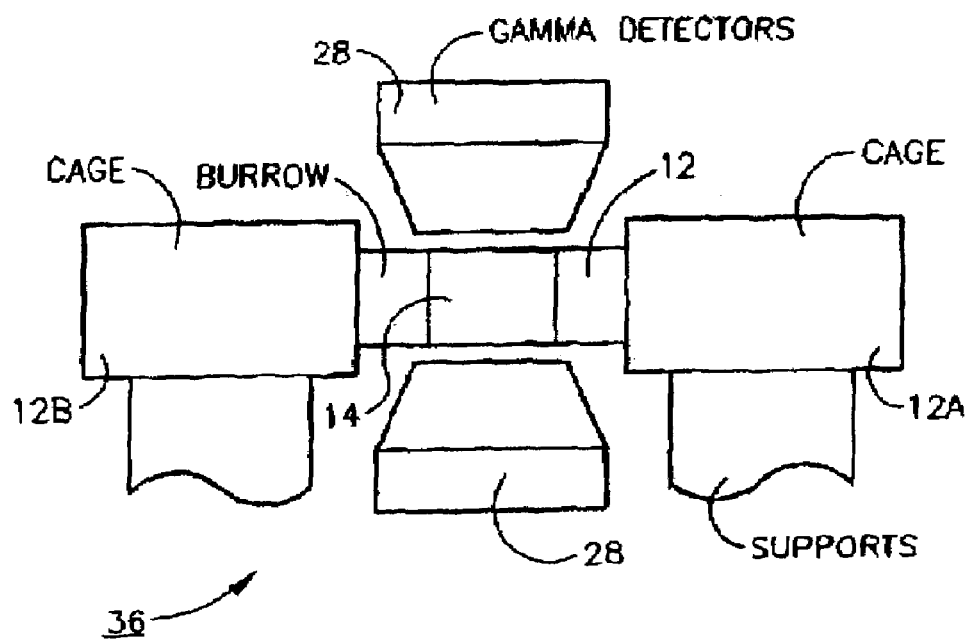
FIG. 3 is a right side view of one embodiment of the imaging apparatus of the present invention.

A variety of laser/CMOS/gamma camera configurations are possible and two of these are depicted in FIGS. 2 and 3. In the configuration depicted in FIG. 2, which is presented looking down burrow 12 with subject 26 facing the direction of the surface of the drawing. In this configuration four gamma detectors 28 are arranged about burrow 12 in a common plane that intersects the gantry's rotational axis with the two lasers 14 and 14A and these are all rotated about burrow 12 to obtain profilometry and gamma imaging of all aspects of subject 26 simultaneously. It is obviously important that the placement of gamma detectors 28 with respect to burrow 12 be such that there is a large enough gap D, identified in FIG. 2, to allow CMOS cameras 20, 20A, 21 and 21A to have an unobstructed view of the entirety of burrow 12 in order that complete profilometry data be obtained. This arrangement of lasers 14 and 14A and gamma detectors 28 is also shown in a more complete form in FIG. 7 that shows a gantry 34 for supporting the various elements of apparatus 36 as well as a cabinet 32 for supporting entire apparatus 36 as well as providing storage for the various electronic and computer components necessary for the operation of apparatus 36.

Figure 4:
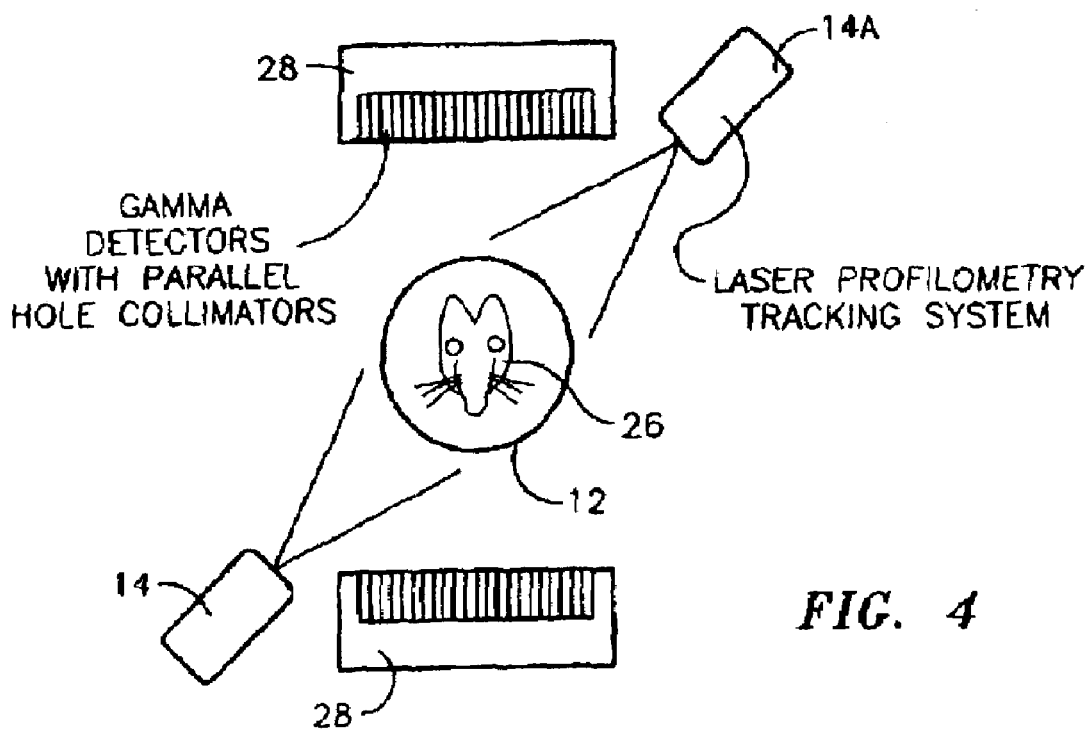
FIG. 4 is a diagrammatic end view of a standard SPECT imaging apparatus in accordance with the present invention.
Figure 5:
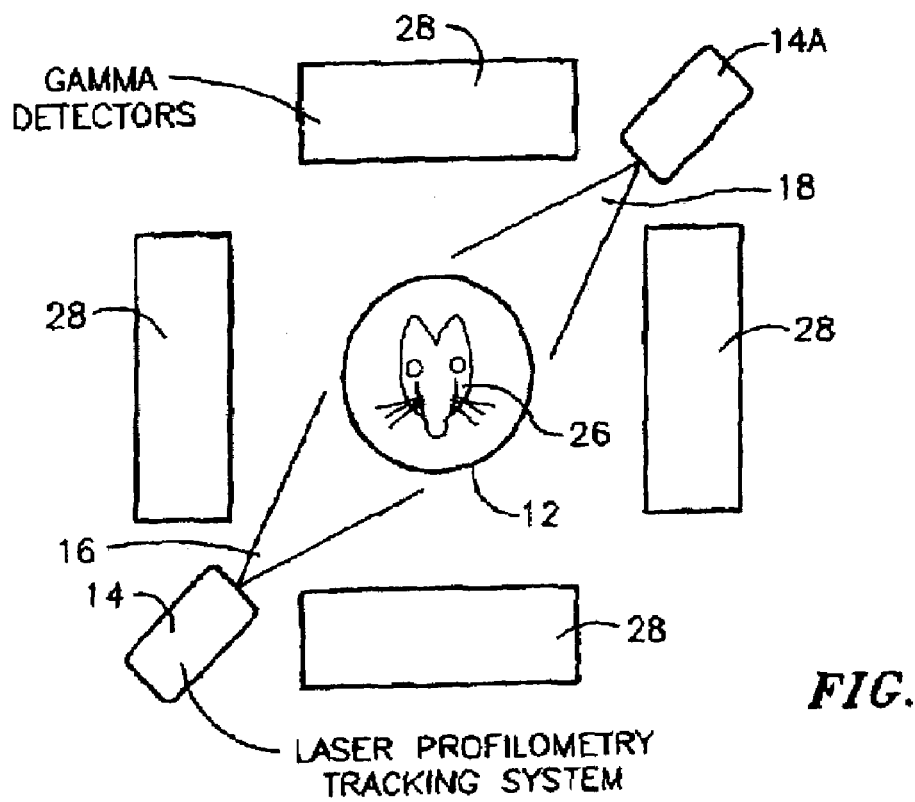
FIG. 5 is a diagrammatic end view of a PET imaging apparatus using two orthogonal gamma detectors in accordance with the present invention.

In the embodiment of the apparatus of the present invention depicted in FIG. 4, only two opposed gamma detectors 28 are utilized for the acquisition of the functional image of subject 26. Again both lasers 14 and 14A and gamma detectors 28 are mounted on a the rotary gantry 34 as depicted in a different view in FIG. 6 that also shows a cabinet 32 upon which gantry 34 is mounted. Cabinet 32 may also be used to store various of the electronic and computer equipment that are necessary to complete operation of apparatus 36.

The PET and SPECT imaging devices 28 may be of any of a number of possible such devices. Recently introduced "mini gamma cameras" using parallel hole collimators as depicted in FIG. 4 are one possible alternative for SPECT imaging while so-called coded aperture masks as discussed by S. R. Meikle et al, "An Investigation of Coded Aperture Imaging for Small Animal SPECT" IEEE Medical Imaging Conference, Lyons, France, 2000 and as depicted schematically in FIG. 2 provide an alternative such SPECT camera configuration. PET imaging can be obtained using more conventional positron imaging device that are well known in the art, for example, the mini-gamma camera described in U.S. Pat. No. 6,271,525 to Majewski et al.

As will be apparent to the skilled artisan, a number of variations and modifications can be made to the system described above without departing from the spirit and scope of the present invention. All such modifications and changes are clearly contemplated as being within the scope of the invention as defined by the appended claims.

What is claimed is:

1. A method for the anatomical and functional imaging of an unrestrained laboratory sized animal strategically labeled with X-ray opaque and IR-laser reflective markers in a non-anesthetized and non-immobilized condition comprising:
   A) injecting or causing the unrestrained laboratory sized animal, a subject, to ingest an appropriate tracer material;
   B) placing the subject in an imaging volume for limited confinement of the subject;
   C) obtaining functional images of the subject by exposure of the subject in an anatomical and functional imaging system comprising:
      I) said imaging volume for limited confinement of the subject;
      II) a gantry about said imaging volume;
      III) a tracking system comprising;
         a) at least two infrared lasers that produce line-shaped IR laser beams that scan across said subject labeled with IR laser reflective markers;
         b) at least two IR sensitive cameras that extract a linear IR laser profile by the acquisition of the image generated by the laser light reflected from the reflective markers and the body of the subject as the cameras sweep across the subject, to spatially locate the subject within the imaging volume and map the body of said subject;
         c) at least two SPECT and PET imaging devices also mounted on said gantry in positions to permit said IR-lasers and said CMOS cameras to view said imaging volume and spatially locate and map said subject while said SPECT and PET imaging devices functionally image said subject through detection of said tracer; and
         d) image processing hardware and software that receive electronic signals from said tracking system and said IR sensitive cameras and generate a combined and registered profile and a functional image of the subject;
   D) either prior or subsequent to said functional imaging obtaining an X-ray CT image of said subject in an anesthetized condition;
   E) integrating said electronic signals from said tracking system and said IR sensitive cameras to generate a combined and registered profile and functional image to produce an integrated functional image of said subject; and
   F) integrating said X-ray CT image and said integrated functional image to produce a combined anatomical and functional image of said subject.

2. The method of claim 1 wherein said IR sensitive camera is a CMOS camera.

3. The method of claim 1 wherein said imaging system includes four IR sensitive cameras.

4. The method of claim 1 wherein said SPECT and PET imaging device includes a parallel hole collimator.

5. The method of claim 1 wherein said SPECT and PET imaging device includes a coded aperture mask.

* * * * *

UNITED STATES PATENT AND TRADEMARK OFFICE
CERTIFICATE OF CORRECTION

PATENT NO.        : 7,209,579 B1
APPLICATION NO.   : 10/341715
DATED             : April 24, 2007
INVENTOR(S)       : Weisenberger et al.

It is certified that error appears in the above-identified patent and that said Letters Patent is hereby corrected as shown below:

Title page, item [73] Assignee: change "Jefferson Solence Ass. LLC" to

--Jefferson Science Associates, LLC--

Signed and Sealed this
Tenth Day of May, 2011

David J. Kappos
*Director of the United States Patent and Trademark Office*